United States Patent [19]
Kao et al.

[11] Patent Number: 5,120,725
[45] Date of Patent: Jun. 9, 1992

[54] BICYCLIC RAPAMYCINS

[75] Inventors: Wenling Kao, Paoli, Pa.; Robert L. Vogel, Stratford, N.J.; John H. Musser, Alameda, Calif.

[73] Assignee: American Home Products Corporation, New York, N.Y.

[21] Appl. No.: 706,811

[22] Filed: May 29, 1991

[51] Int. Cl.[5] .................. A61K 31/395; C07D 491/06
[52] U.S. Cl. ................................. 514/183; 314/321; 540/456
[58] Field of Search ............... 540/456; 514/183, 321

[56] References Cited
U.S. PATENT DOCUMENTS
3,929,992 12/1975 Sehgal et al. .................. 424/122

OTHER PUBLICATIONS
Can. J. Physiol. Pharmacol. 55, 48 (1977).

*Primary Examiner*—Robert T. Bond
*Attorney, Agent, or Firm*—Walter Patton

[57] ABSTRACT

A bicyclic derivative of rapamycin of general formula (1)

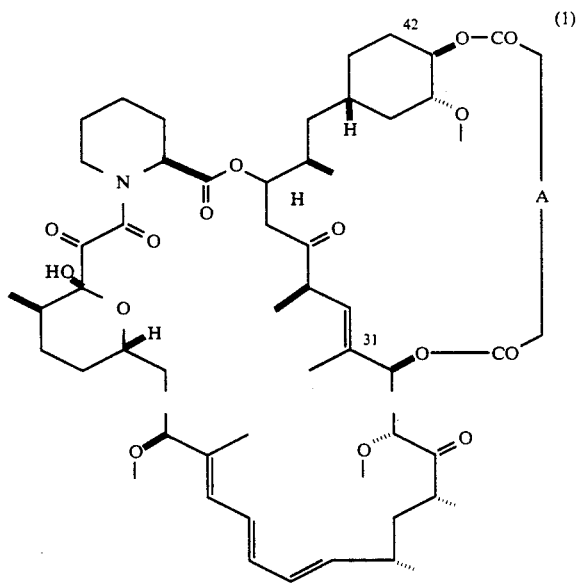

wherein

A is $-(CH_2)_n$, or $-(CH_2)_n-(CH=CH)-(CH_2)_m-$, or $-(CH_2)_n-(CH\equiv CH)-(CH_2)_m-$, or

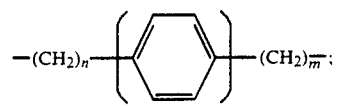

$n = 2$ to $10$,
$m = 2$ to $10$ and
$n = m$ or $n \neq m$
or a pharmaceutically acceptable salt thereof, which is by virtue of its immunosuppressive activity is useful in treating transplantation rejection host vs. graft disease, autoimmune diseases, and diseases of inflammation.

6 Claims, No Drawings

BICYCLIC RAPAMYCINS

BACKGROUND OF THE INVENTION

This invention relates to bicyclic rapamycins and a method for using them in the treatment of transplantation rejection, host vs. graft disease, autoimmune diseases, diseases of inflammation, solid tumors, and fungal infections.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Seghal et al., J. Antibiot. 28, 727 (1975); H. A. Baker et al., J. Antibiot. 31, 539 (1978); U.S. Pat. No. 3.922,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55,48 (1976)] disclosed that rapamycin is effective in the experimental allergic encephalomyelitis model, a model for multiple sclerosis; in the adjuvant arthritis model, a model for rheumatoid arthritis; and effectively inhibited the formation of IGE-like antibodies.

The immunosuppressive effects of rapamycin have been disclosed in FASEB 3, 3411 (1989), rapamycin has been shown to be effective in inhibiting transplant rejection (U.S. Patent Application Ser. No. 362,544 filed Jun. 6, 1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42- positions.

DESCRIPTION OF THE INVENTION

This invention relates to bicyclic rapamycins of general formula (1), which possess immunosuppressive and/or antifungal and/or antitumor and/or antiinflammatory activity in vivo and/or inhibit thymocyte proliferation in vitro and are therefore useful in the treatment of transplantation rejection, autoimmune diseases (i.e. lupus, rheumatoid arthritis, diabetes mellitus, multiple sclerosis), fungal infections (i.e. Candida albicans), cancer, and diseases of inflammation

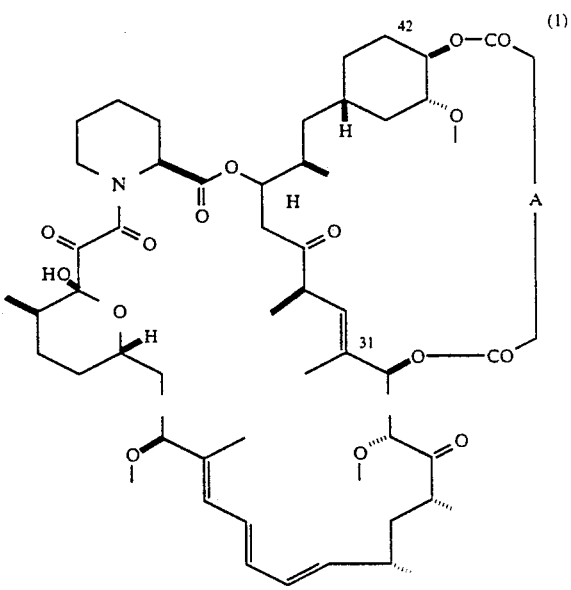

wherein

A is $-(CH_2)_n-$, or $-(CH_2)_n-(CH=CH)-(CH_2)_m-$, or $-(CH_2)_n-(CH\equiv CH)-(CH_2)_m-$, or

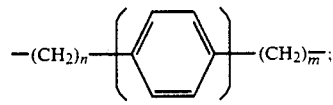

n = 2 to 10, m = 2 to 10 and n = m or n ≠ m or a pharmaceutically acceptable salt thereof.

The bicyclic rapamycins of general formula (1) of this invention can be synthesized by reaction of rapamycin with diacyl halides at elevated temperature (30°–70° C.) in pyridine.

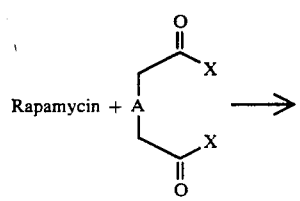

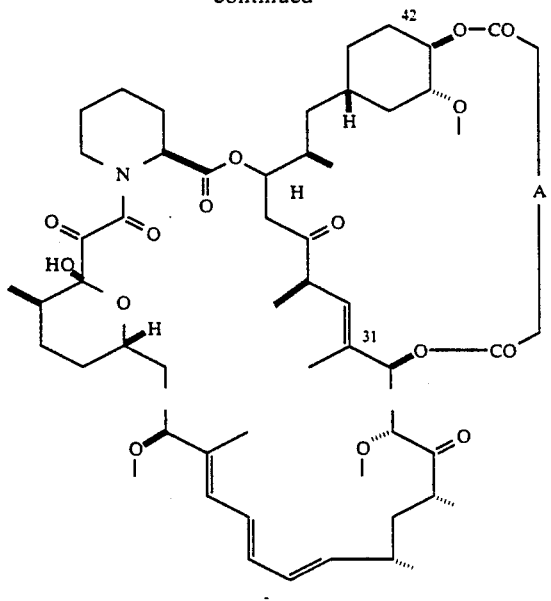

where X is halogen and A is as defined above.

The pharmaceutically acceptable salts may be formed from inorganic cations such as sodium, potassium, and the like.

PRIOR ART

The ester formation between alcohol and acyl halide has been described [Jerry March, Advanced Organic Chemistry, 3rd edition, published in 1985, page 346]. The specific reaction condition employed in this invention was developed by S. Rakhit of Ayerst Laboratories and reported in U.S. Pat. No. 4,316,885 Feb. 23, 1982).

Immunosuppresive activity of the compounds of the present invention was evaluated in an in vitro standard pharmacological test procedure to measure lymphocyte proliferation (LAF).

The comitogen-induced thymocyte proliferation procedure (LAF) was used as an in vitro measure of the immunosuppressive effects of representative compounds. Briefly, cells from the thymus of normal BALB/c mice were cultured for 72 hours with PHA and IL-1 and pulsed with tritiated thymidine during the last six hours. Cells are cultured with and without various concentrations of rapamycin, cyclosporin A, or test compound. Cells are harvested and incorporated; radioactivity is determined. Inhibition of lymphoproliferation is assessed in percent change in counts per minute from non-drug treated controls. The results are expressed by the following ratio:

$$\frac{^3\text{H-control thymus cells} - \text{H}^3\text{-rapamycin-treated thymus cells}}{^3\text{H-control thymus cells} - \text{H}^3\text{-test compound-treated cells}}$$

The following table summarizes the results of representative compounds of this invention in this test procedure.

TABLE 1

| | Biological Activity - LAF Assay | |
|---|---|---|
| | R/*A at 100 nM | at 10 nM |
| Example 1 | 0.10 | 0.03 |
| Example 2 | 0.45 | 0.06 |
| Example 3 | 0.46 | 0.03 |

*Relative potency of analogs/rapamycin at dosages 100 nM and at 10 nM.

The results of this standard pharmacological test procedure for a representative compound of this invention demonstrates that the compounds of this invention are useful as immunosuppressive agents.

The compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

The following examples illustrate the preparation of representative compounds of this invention.

EXAMPLE 1

Rapamycin-31,42-cyclic diester with heptanedioic acid

A solution of 2.0 g pimeloyl chloride in 2 mL toluene was added to a solution of 5.0 g rapamycin in 250 mL dry toluene and 5 mL pyridine, and the resulting mixture was heated at 50°-55° C. under nitrogen for 65 hours, then cooled to ambient temperature, diluted with 100 mL ethyl acetate and treated with 50 mL 2N HCl and 200 mL brine. The organic portion was washed with brine, dried over MgSO₄ and stripped of solvent. Chromatography through silica gel using a gradient of 0.5% to 10% methanol in dichloromethane yielded an early fraction (200 mg) that contained desired product and a byproduct (M.S.). Further chromatography of that fraction on silica gel using a gradient of 20% to 30% ethyl acetate in dichloromethane yielded 40 mg of the title compound as a light tan solid, mp 107°-121° C.

IR (KBr): 3420, 2930, 1735, 1647, 1460 and 990 cm$^{-1}$. NMR (CDCl$_3$, 400 MHz): δ 3.38 to 3.34 (broad, 6H, two OMe's), 3.16 (3H, OMe), MS (neg FAB): 1037 (M—).

EXAMPLE 2

Rapamycin-31,42-cyclic diester with hexanedioic acid

Adipoyl chloride (0.80 g) was added to a solution of 2.0 rapamycin in 50 mL toluene and 1 mL pyridine and heated at 50° C. under nitrogen for 90 hours. The reaction mixture was cooled to ambient temperature, diluted with 50 mL ethyl acetate, and treated with 20 mL 2N HCl and 50 mL brine. The aqueous portion was extracted with ethyl acetate; the organic portion was dried over MgSO₄ and stripped to a yellowbrown solid foam. Chromatography through silica gel beginning with dichloromethane followed by a methanol gradient of 0.5% to 3% in dichloromethane yielded 50 mg product as a yellow solid, mp 105°-115° C.

IR (KBr): 3430, 2930, 1742, 1658, 1460 and 988 cm$^{-1}$. NMR (CDCl$_3$, 400 MHz): δ 3.31 (broad, 6H, two OMe's), 3.11 (3H, OMe). MS (neg FAB): 1023 (M—).

EXAMPLE 3

Rapamycin-31,42-cyclic diester with octanedioic acid

Suberoyl chloride (0.80 g) was added to a solution of 2.0 rapamycin in 50 mL toluene and 1 mL pyridine and heated at 50° C. under nitrogen for 92 hours. The reaction mixture was cooled to ambient temperature, diluted with 50 mL ethyl acetate, and treated with 20 mL 2N HCl and 50 mL brine. The aqueous portion was extracted with ethyl acetate; the organic portion was dried over MgSO₄ and stripped to a yellowbrown solid foam. Chromatography through silica gel beginning with dichloromethane followed by a methanol gradient of 0.5% to 3% in dichloromethane yielded 110 mg product as a pale yellow solid, mp 86°-99° C.

IR (KBr): 3430, 2930, 1730, 1450 and 990 cm$^{-1}$. NMR (CDCl$_3$, 400 MHz): δ 3.32-3.29 (broad, 6H, two OMe's), 3.10 (3H, OMe). MS (neg FAB): 1051 (M—).

What is claimed is:

1. A bicyclic rapamycin of formula (1)

wherein

A is —(CH$_2$)$_n$, or

—(CH$_2$)$_n$—(CH=CH)—(CH$_2$)$_m$—, or

—(CH$_2$)$_n$—(C≡CH)—(CH$_2$)$_m$—, or

—(CH$_2$)$_n$—⟨C$_6$H$_4$⟩—(CH$_2$)$_m$—;

n = 2 to 10, m = 2 to 10 and n = m or n ≠ m or a pharmaceutically acceptable salt thereof.

2. A compound of claim 1 wherein A is —(CH$_2$)$_4$— or a pharmaceutically acceptable salt thereof.

3. A compound of claim 1 wherein A is —(CH$_2$)$_5$— or a pharmaceutically acceptable salt thereof.

4. A compound of claim 1 wherein A is —(CH$_2$)$_6$— or a pharmaceutically acceptable salt thereof.

5. A method of treating transplantation rejection, host vs. graft disease, autoimmune diseases, and diseases of inflammation in a mammal by administering an effective amount of a compound which is a bicyclic rapamycin of formula (1)

-continued

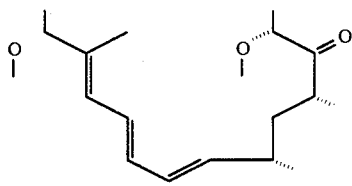

wherein

A is —(CH$_2$)$_n$, or

—(CH$_2$)$_n$—(CH=CH)—(CH$_2$)$_m$—, or

—(CH$_2$)$_n$—(CH≡CH)—(CH$_2$)$_m$—, or

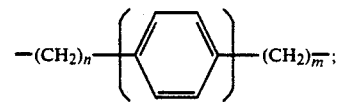

n=2 to 10,
m=2 to 10 and
n=m or n≠m
or a pharmaceutically acceptable salt thereof.

6. A pharmaceutical composition useful for treating transplantation rejection, host vs. graft disease, autoimmune diseases, and diseases of inflammation in a mammal comprising an effective amount of a compound of claim 1 or a pharmaceutically acceptable salt thereof and a pharmaceutically acceptable carrier.

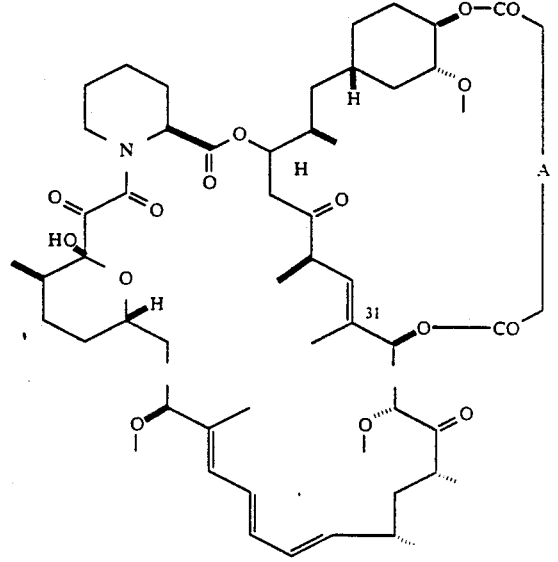

(1)

* * * * *